(12) United States Patent
Holder et al.

(10) Patent No.: US 11,407,970 B2
(45) Date of Patent: Aug. 9, 2022

(54) AUTOMATED BACTERIA IDENTIFICATION AND ANTIBIOTIC SUSCEPTIBILITY PROFILING DEVICE

(71) Applicant: The Charles Stark Draper Laboratory, Inc., Cambridge, MA (US)

(72) Inventors: Jason Holder, Swampscott, MA (US); Parker Dow, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 683 days.

(21) Appl. No.: 16/428,376

(22) Filed: May 31, 2019

(65) Prior Publication Data
US 2019/0367863 A1    Dec. 5, 2019

Related U.S. Application Data

(60) Provisional application No. 62/679,617, filed on Jun. 1, 2019.

(51) Int. Cl.
| | | |
|---|---|---|
| *C12M 1/36* | (2006.01) |
| *C12M 1/32* | (2006.01) |
| *C12M 1/00* | (2006.01) |
| *C12M 1/42* | (2006.01) |
| *C12M 1/34* | (2006.01) |
| *C12Q 1/04* | (2006.01) |
| *C12M 3/06* | (2006.01) |
| *G01N 35/10* | (2006.01) |

(52) U.S. Cl.
CPC ............ *C12M 41/48* (2013.01); *C12M 23/12* (2013.01); *C12M 23/50* (2013.01); *C12M 27/16* (2013.01); *C12M 35/04* (2013.01); *C12M 41/40* (2013.01); *C12M 41/42* (2013.01); *C12M 41/46* (2013.01); *C12Q 1/04* (2013.01); *G01N 35/10* (2013.01)

(58) Field of Classification Search
CPC ............................... C12M 41/48; G01N 35/10
See application file for complete search history.

(56) References Cited

U.S. PATENT DOCUMENTS

| | | | | |
|---|---|---|---|---|
| 2010/0126286 | A1* | 5/2010 | Self | G01N 35/026 73/863.81 |
| 2018/0088141 | A1* | 3/2018 | Vacic | G01N 35/028 |
| 2018/0127695 | A1* | 5/2018 | Nam | C12M 41/36 |
| 2020/0025782 | A1* | 1/2020 | Ahlfors | G01N 35/0099 |

* cited by examiner

*Primary Examiner* — Jonathan M Hurst
(74) *Attorney, Agent, or Firm* — Foley & Lardner LLP

(57) ABSTRACT

Systems and methods of testing a fluid sample are provided. A method can include controlling an orientation of a loader including a sample holder configured to hold a sample vessel to correspond to a first predetermined tilt angle. The method can include controlling an articulator to transfer the fluid sample from the sample vessel to at least one well of a plurality of wells of a multiwell plate positioned on a plate deck within the enclosure. The method can include controlling the articulator to move the multiwell plate to a hotel incubator within the enclosure. The method can include applying a bacteriophage to the fluid sample. The method can include controlling the articulator to move the multiwell plate from the hotel incubator to a testing system within the enclosure after a predetermined reaction time period. The method can include receiving output data from the testing system.

20 Claims, 17 Drawing Sheets

AUTOMATED BACTERIA IDENTIFICATION AND ANTIBIOTIC SUSCEPTIBILITY PROFILING DEVICE

CROSS-REFERENCE TO RELATED APPLICATION

This application claims priority to U.S. Provisional Patent Application No. 62/679,617, filed on Jun. 1, 2018 and entitled "AUTOMATED BACTERIA IDENTIFICATION AND ANTIBIOTIC SUSCEPTIBILITY PROFILING DEVICE," which is hereby incorporated by reference in its entirety.

BACKGROUND OF THE DISCLOSURE

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days. Additionally, some bacterial strains are not amenable to culturing and in vitro analysis in light of their fastidious nature. In other situations, the observable behavior of some bacterial strains is not readily distinguishable from others. Moreover, individual strains of a particular bacterial species may exhibit resistance to otherwise effective antibiotics.

Early and accurate identification of the bacterial strain(s) responsible for a patient's illness and determining its susceptibility to various antibiotics is an important aspect of the treatment selection decision process.

SUMMARY OF THE DISCLOSURE

The present disclosure describes a fully automated system for the execution of bacteria identification and antibiotic susceptibility test (IDAST) reactions. The system can automatically cycle between growth and sampling modes. In a growth mode, the system can increase a number of bacteria cells a given sample. During sample mode, the system can perform tests on the sample (or a portion thereof). For a given input sample, the system can continuously grow and test the sample to run a large number of tests. The tests can identify bacteria in the sample and profile the species of the bacteria. The system can also automatically test the bacteria's response to different levels of different antibiotics. The system can generate, based on the bacteria's response to the antibiotics, accurate Minimal Inhibitory Concentration (MIC) and Sensitive, Intermediate, and Resistant (SIR) classifications.

At least one aspect of this disclosure is directed to a system for testing a fluid sample. The system can include an enclosure. The system can include a loader positioned within the enclosure and including a sample holder configured to hold a sample vessel. The system can include a plate deck positioned within the enclosure and configured to support a multiwell plate including a plurality of wells. The system can include a hotel incubator positioned within the enclosure and configured to receive the multiwell plate. The system can include an articulator positioned within the enclosure and configured to manipulate and transfer the fluid sample within the system. The system can include a testing system positioned within the enclosure and configured to identify bacteria in the fluid sample. The system can include a controller configured to operate the system in a growth mode by controlling an orientation of the loader to correspond to a first predetermined tilt angle with respect to a base of the enclosure to cause the bacteria to grow in the fluid sample within the sample vessel for a predetermined growth time period. The controller can be configured to operate the system in a sampling mode by controlling the articulator to transfer the fluid sample from the sample vessel to at least one well of the plurality of wells of the multiwell plate. The controller can be configured to control the articulator to move the multiwell plate from the plate deck to the hotel incubator. The controller can be configured to apply a bacteriophage to the fluid sample. The controller can be configured to control the articulator to move the multiwell plate from the hotel incubator to the testing system after a predetermined reaction time period. The controller can be configured to receive output data from the testing system. The output data can identify a characteristic of the bacteria in the fluid sample.

In some implementations, the system can include an environmental control system configured to control at least one environmental characteristic within the enclosure. In some implementations, the environmental control system can include a vacuum pump. In some implementations, the controller can be further configured to control the vacuum pump to maintain a predetermined pressure within the enclosure. In some implementations, the environmental control system can include a gas pump. In some implementations, the controller can be further configured to control the gas pump to circulate a gas within the enclosure.

In some implementations, the controller can be further configured to control the orientation of the loader to correspond to a second predetermined tilt angle, different from the first predetermined tilt angle, with respect to a base of the enclosure during the sampling mode. In some implementations, the second predetermined tilt angle of the loader can be perpendicular to the base of the enclosure.

In some implementations, the loader can further include a shaker. In some implementations, the controller is further configured to cause the shaker to vibrate the sample holder to agitate the fluid sample during the growth mode.

In some implementations, the articulator can further include an automated liquid handling pipette to transfer the fluid sample from the sample holder to the at least one well of the plurality of wells of the multiwell plate. In some implementations, the articulator can further include a plate gripper to move the multiwell plate from the plate deck to the hotel incubator.

In some implementations, the hotel incubator can further include at least one slot configured to receive the multiwell plate. In some implementations, the hotel incubator can further include a heating element coupled with the at least one slot and configured to apply heat to multiwell plate within the at least one slot.

In some implementations, the bacteriophage can include a lumi-phage. In some implementations, the testing system can be configured to measure light emitted by the bacteriophage.

In some implementations, the system can further include a filtering system configured to receive the fluid sample and to remove particles from the fluid sample. In some implementations, the controller can be further configured to cause the filtering system to remove the particles from the fluid sample using at least one acoustophoresis, membrane-based filtering, or chemical filtering.

In some implementations, the system can further include an antibiotic within the at least one well of the multiwell plate. In some implementations, the controller can be further configured to process the output data received from the testing system to determine a response of the bacteria to the antibiotic. In some implementations, the fluid sample can include a first fluid sample. In some implementations, the controller can be further configured to cause the system to process a second fluid sample simultaneously with the first fluid sample.

Another aspect of this disclosure is directed to a method of testing a fluid sample. The method can include controlling, by a controller including at least one processor, an orientation of a loader including a sample holder configured to hold a sample vessel to correspond to a first predetermined tilt angle with respect to a base of an enclosure to cause bacteria to grow in the fluid sample during a predetermined growth time period. The method can include controlling, by the controller, an articulator to transfer the fluid sample from the sample vessel to at least one well of a plurality of wells of a multiwell plate positioned on a plate deck within the enclosure. The method can include controlling, by the controller, the articulator to move the multiwell plate from the plate deck to a hotel incubator within the enclosure. The method can include applying a bacteriophage to the fluid sample. The method can include controlling, by the controller, the articulator to move the multiwell plate from the hotel incubator to a testing system within the enclosure after a predetermined reaction time period. The method can include receiving, by the controller, output data from the testing system. The output data can identify a characteristic of the bacteria in the fluid sample.

In some implementations, the method can include controlling, by the controller, an environmental control system configured to control at least one environmental characteristic within the enclosure. In some implementations, the environmental control system can include a vacuum pump. In some implementations, the method can further include controlling the vacuum pump to maintain a predetermined pressure within the enclosure. In some implementations, the environmental control system can include a gas pump. In some implementations, the method can further include controlling the gas pump to circulate a gas within the enclosure.

In some implementations, the loader can further include a shaker. In some implementations, the method can further include causing the shaker to vibrate the sample holder to agitate the fluid sample during the growth mode.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present solution includes a fully automated system for the execution of bacteria IDAST reactions. The system enables the growth of samples to increase the number of cells to enable the system to run a large number of tests. The test can identify bacteria in the sample and profile the species of the bacteria. The system can also automatically test the bacteria's response to different levels of different antibiotics. The system can generate, based on the bacteria's response to the antibiotics, accurate Minimal Inhibitory Concentration (MIC) and Sensitive, Intermediate, and Resistant (SIR) classifications.

Figure 1:
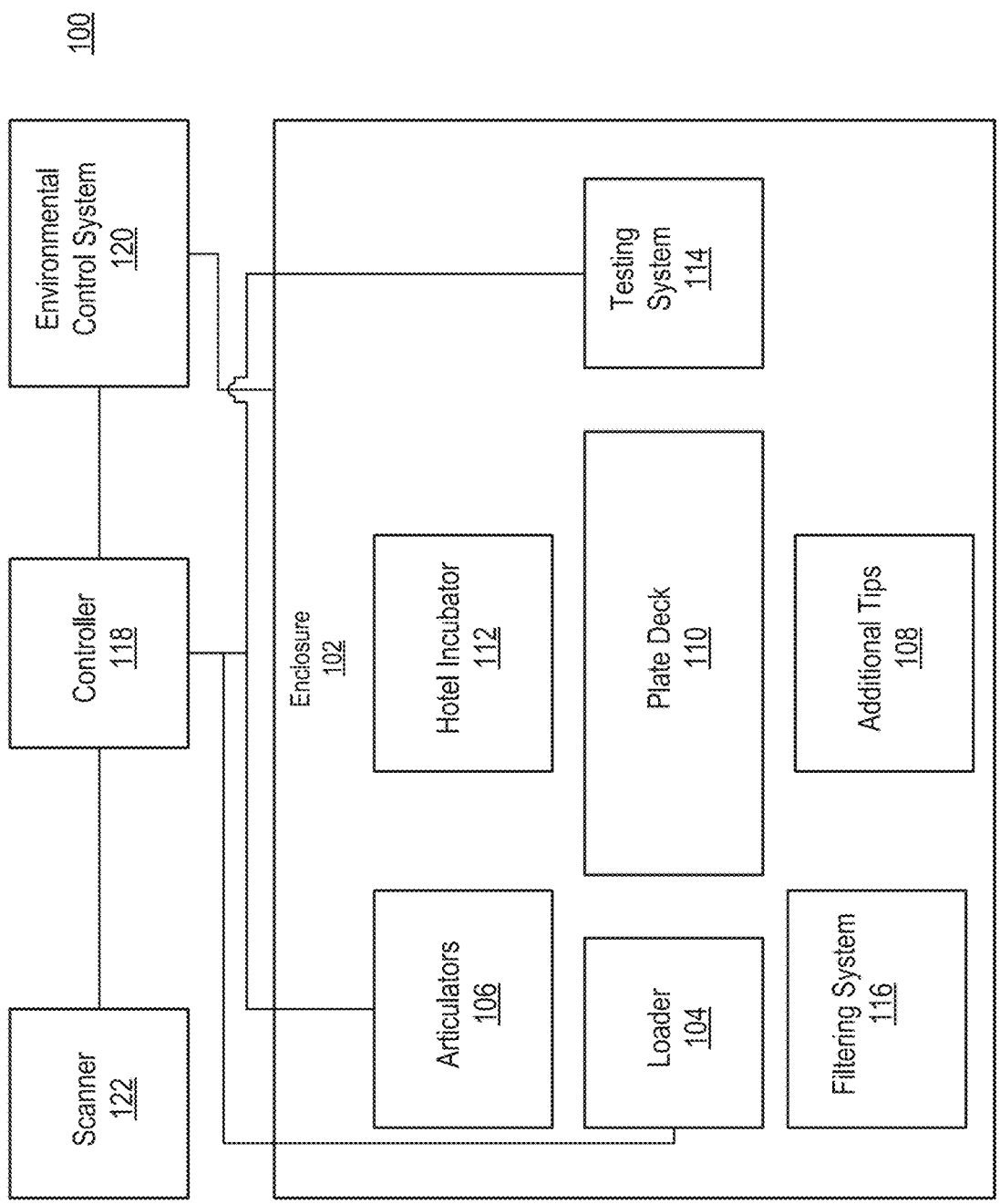
FIG. 1 illustrates a block diagram of an example system to automatically test fluid samples, according to an illustrative implementation.
Figure 2:
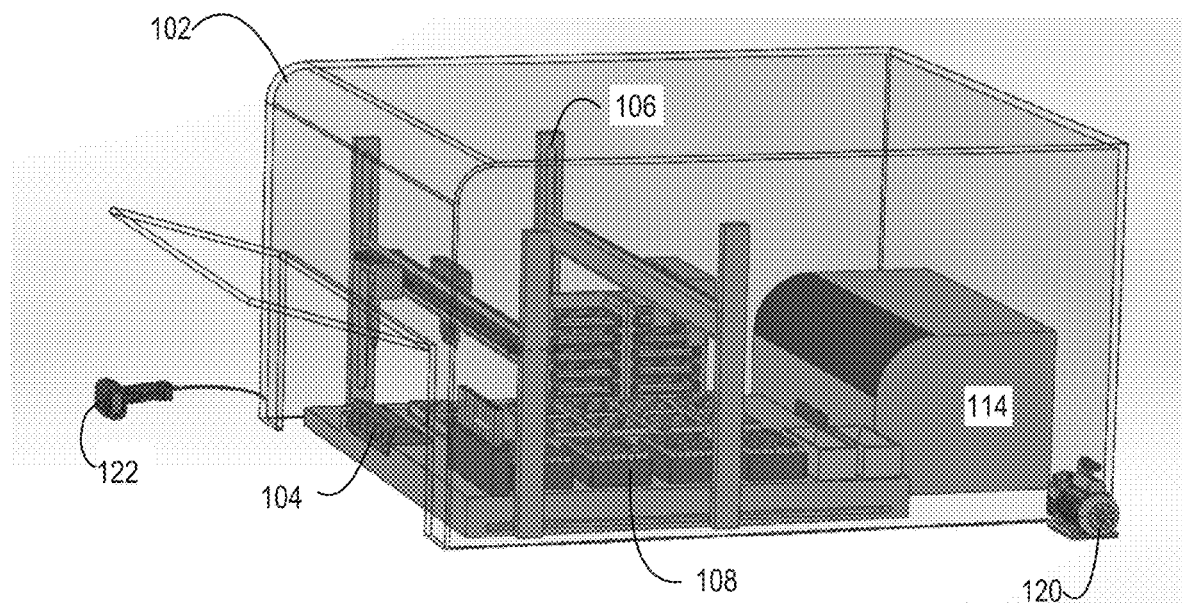
FIGS. 2-15 illustrate various views of example embodiments of the system illustrated in FIG. 1, according to illustrative implementations.
Figure 3:
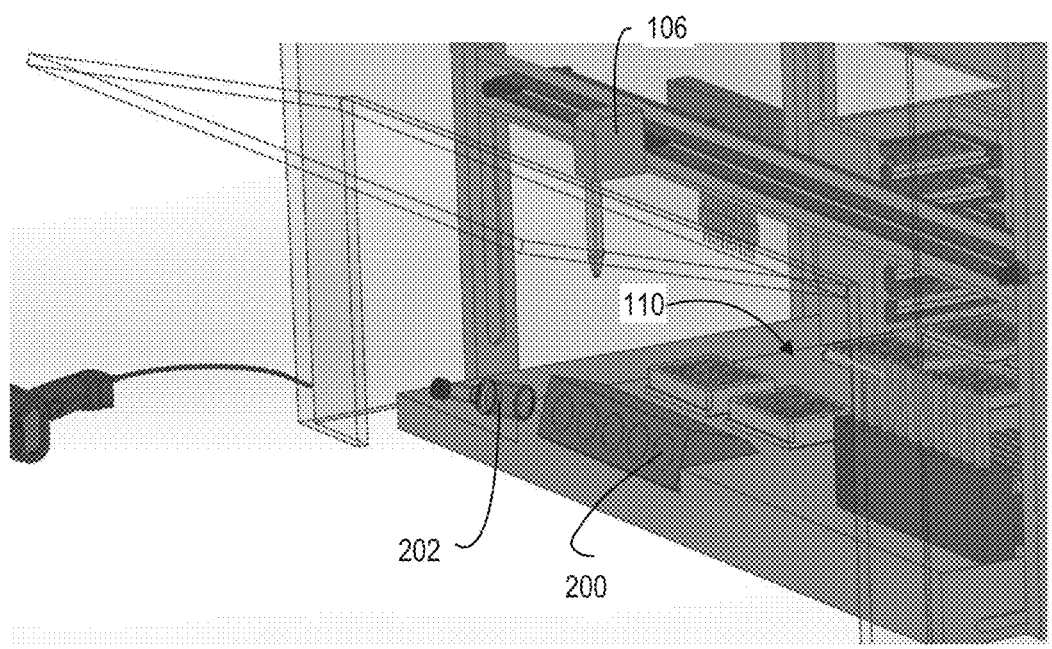

FIG. 1 illustrates a block diagram of an example system 100 to automatically perform IDAST reactions. FIGS. 2-15 illustrate various views of example embodiments of the system 100 illustrated in FIG. 1, according to illustrative implementations. Referring now to FIGS. 1-15, the system 100 includes an enclosure 102. Within the enclosure 102, the system 100 includes a loader 104. One or more articulators 106 can move samples from the loader 104 to the other areas of the system, such as the plate deck 110, hotel incubator 112, and testing system 114. The system 100 can include a location for additional tips 108. The system 100 can include a filtering system 116. The system 100 can include a controller 118 that can control the testing system 114, the environmental control system 120, and the scanner 122.

The system 100 can include an enclosure 102. The enclosure 102 can be a sealed or partially sealed enclosure. The enclosure 102 can include one or more doors to enable samples to be loaded into the loader 104. The enclosure 102 can include windows that enable visualization of the components inside the enclosure 102 or one or more of the enclosure's walls can be clear. The enclosure 102 can maintain environmental conditions that support the growth and proliferation of the cells within the samples. The environmental conditions can include temperature, humidity, gas mixtures (e.g., oxygen and CO2 mixtures) and concentrations, and gas pressure within the enclosure 102. The environmental conditions can be set and maintained via the environmental control system 120. The environmental control system 120 can include one or more gas pumps that circulate gas through the enclosure 102. The environmental control system 120 can include one or more heaters that maintains a predetermined temperature within the enclosure 102. For example, the environmental control system 120 can control heating elements within the enclosure 102 or within the hotel incubator 112, or with both the enclosure 102 and the hotel incubator 112. In some implementations, the environmental control system 120 can maintain a negative pressure within the enclosure 102 such that contaminants, cells, and other particles do not escape the enclosure 102. For example, when the enclosure's door is opened, because of the negative pressure, air flows into the enclosure 102 and not out of the enclosure 102.

For example, the enclosure 102 can control the escape of particles to ensure that no biological organisms exit the testing environment within the enclosure 102. The environmental control system 120 can include a vacuum pump to maintain a negative pressure within the enclosure 102. Samples, such as bacteriophages and infectious microbes can be opened inside the controlled environment of the enclosure 102 and at the end of the processes performed by the system 100, the system can chemically kill the samples with strong detergents, bleach, metal chelators, and UV light exposure.

Figure 4:
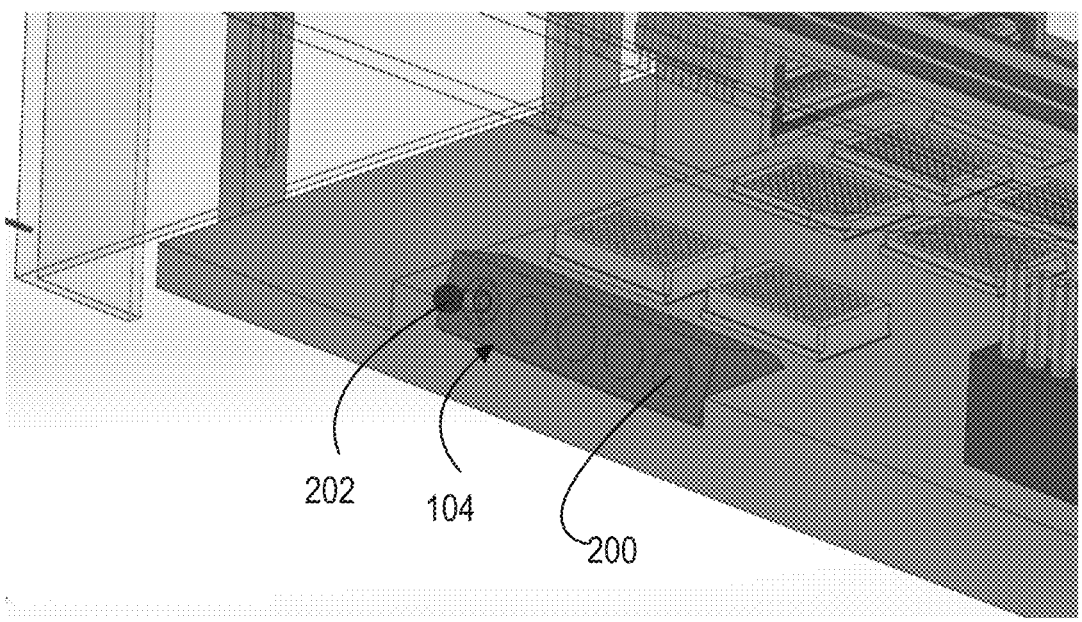

The system 100 can include a loader 104. The loader 104 can include a plurality of sample holders 200 that are each configured to hold a sample vessel 202, which can be a blood bottle. The system 100 can operate in both a growth mode and a sample mode. During the growth mode, the loader 104 can be tilted at an angle with respect to the base of the enclosure 102, as illustrated in FIG. 4. The loader 104 can include an orbital or other shaker. The loader 104 can shake, rotate, or otherwise agitate the sample. Agitation of the sample, via the loader 104, can expose the sample within the sample vessel 202 to oxygen or the other gases within the enclosure 102.

The system 100 can continue in the growth mode until enough cells are available in the sample to perform a desired test. The system 100 can continue in the growth mode for a predetermined amount of time. The growth mode can enable the system 100 to diagnose low-titer patient samples such as blood. The system 100 can continue in the growth mode until a sample is withdrawn from the sample vessel 202. The growth mode can be interrupted for sampling and reactions assembly followed by initiation of another cycle of the growth mode.

Figure 5:
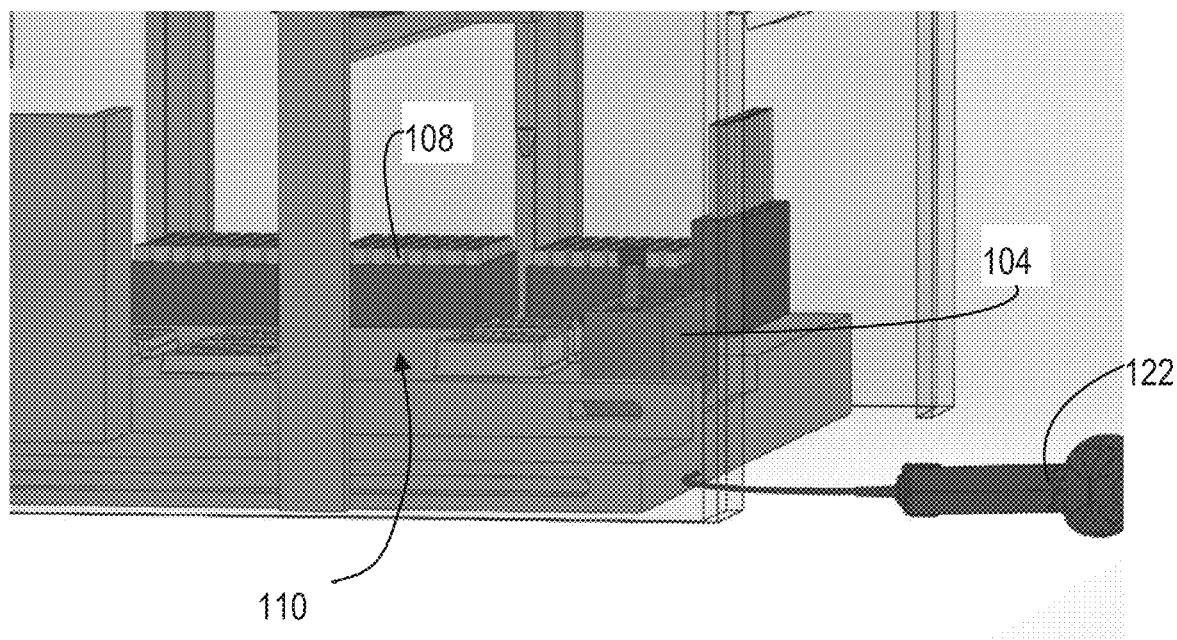
Figure 6:
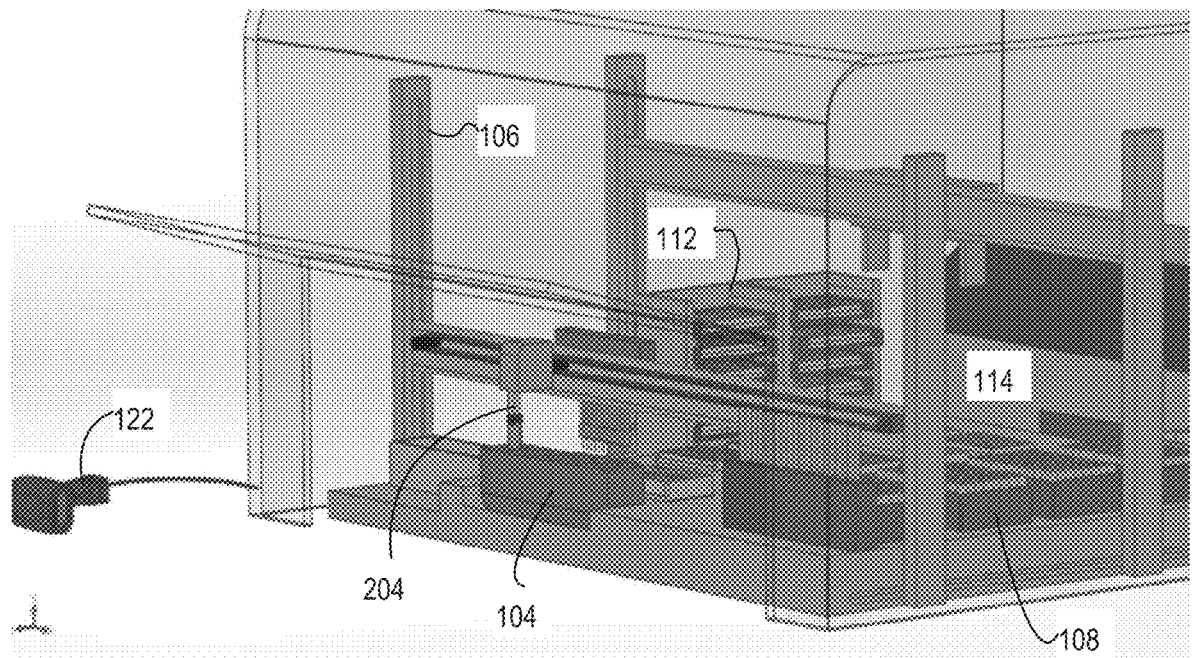
Figure 7:
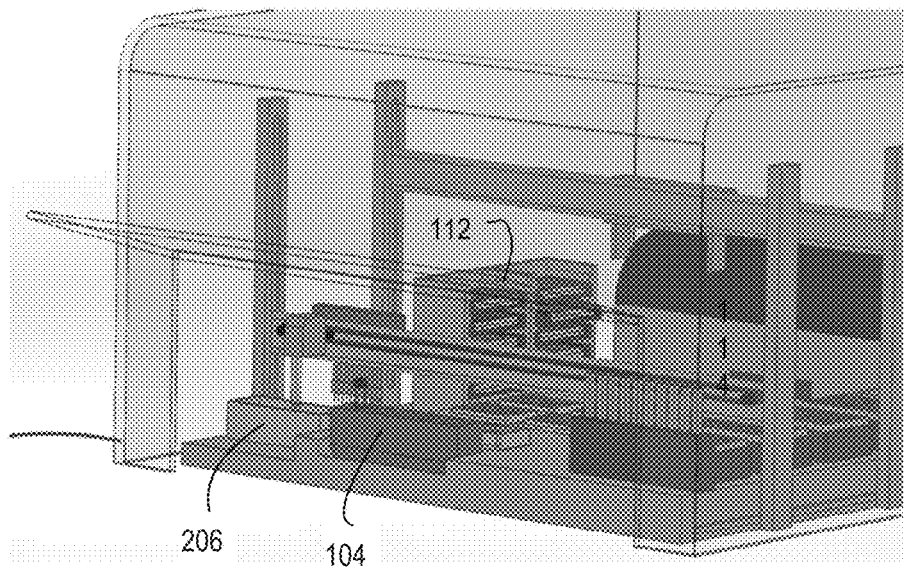
Figure 8:
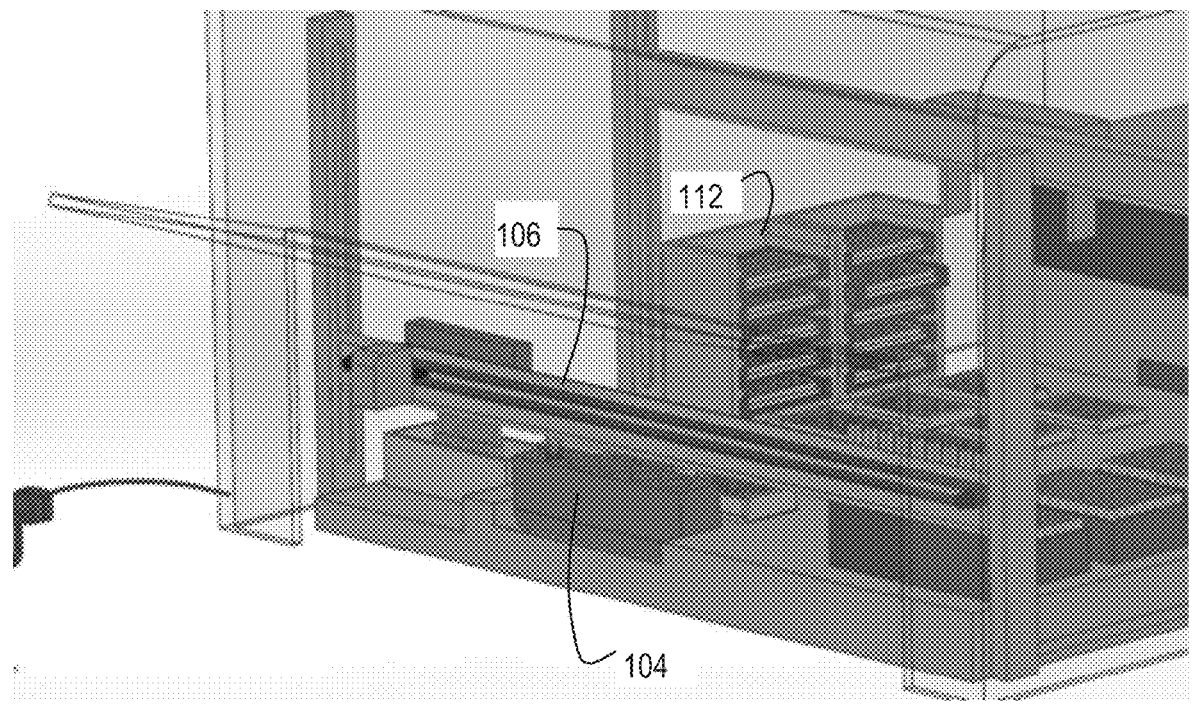
Figure 9:
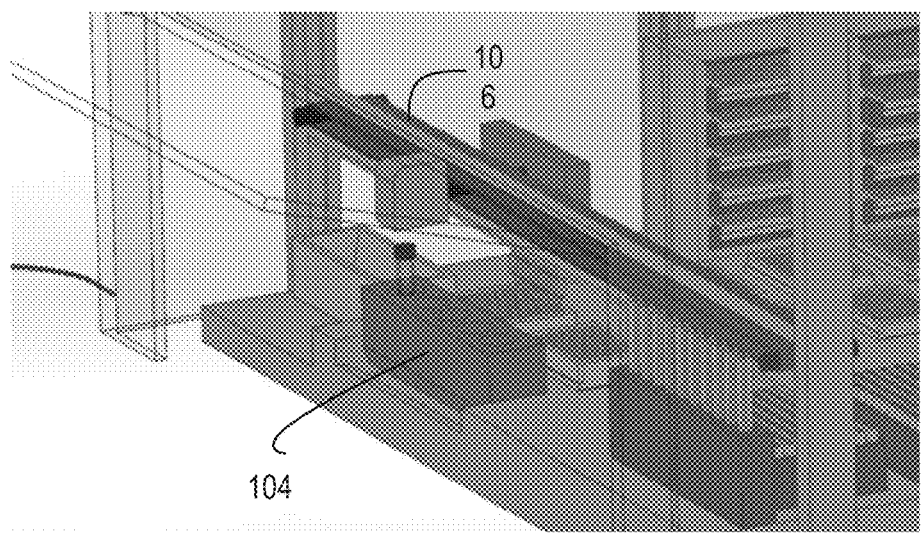
Figure 10:
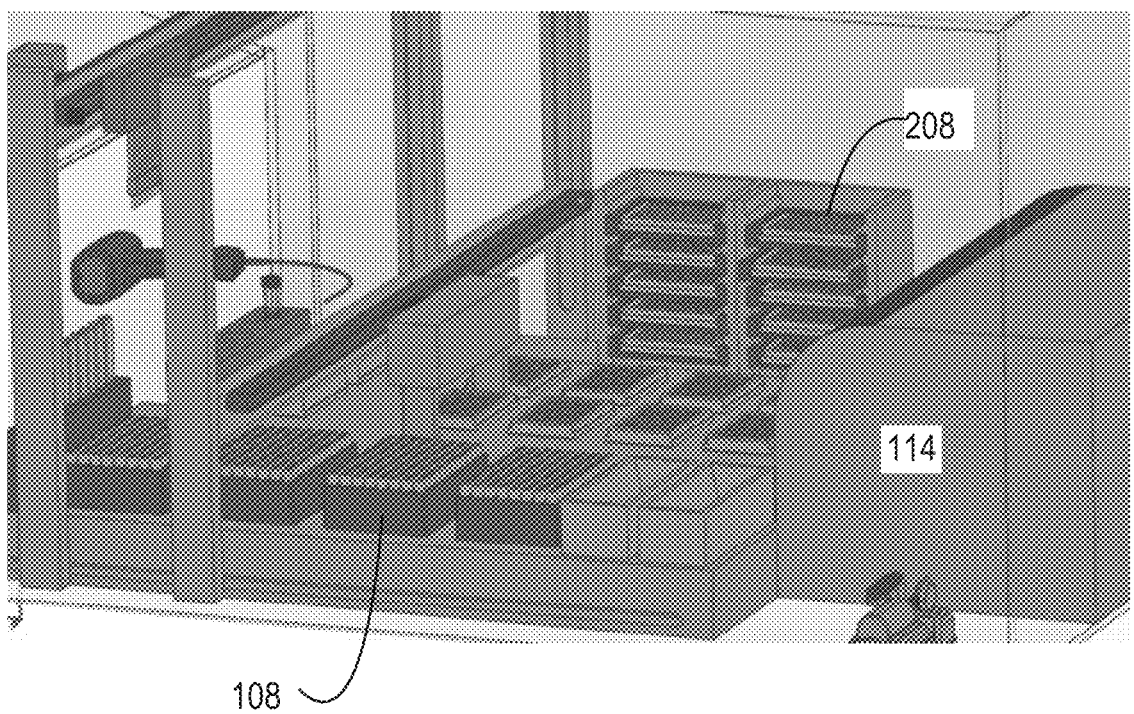
Figure 11:
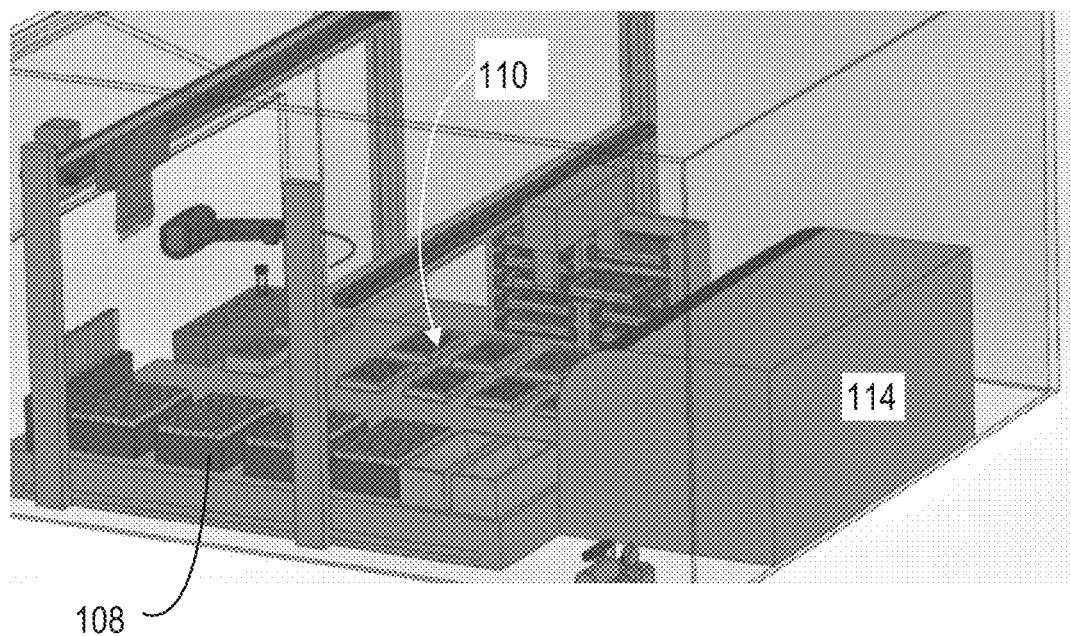
Figure 12:
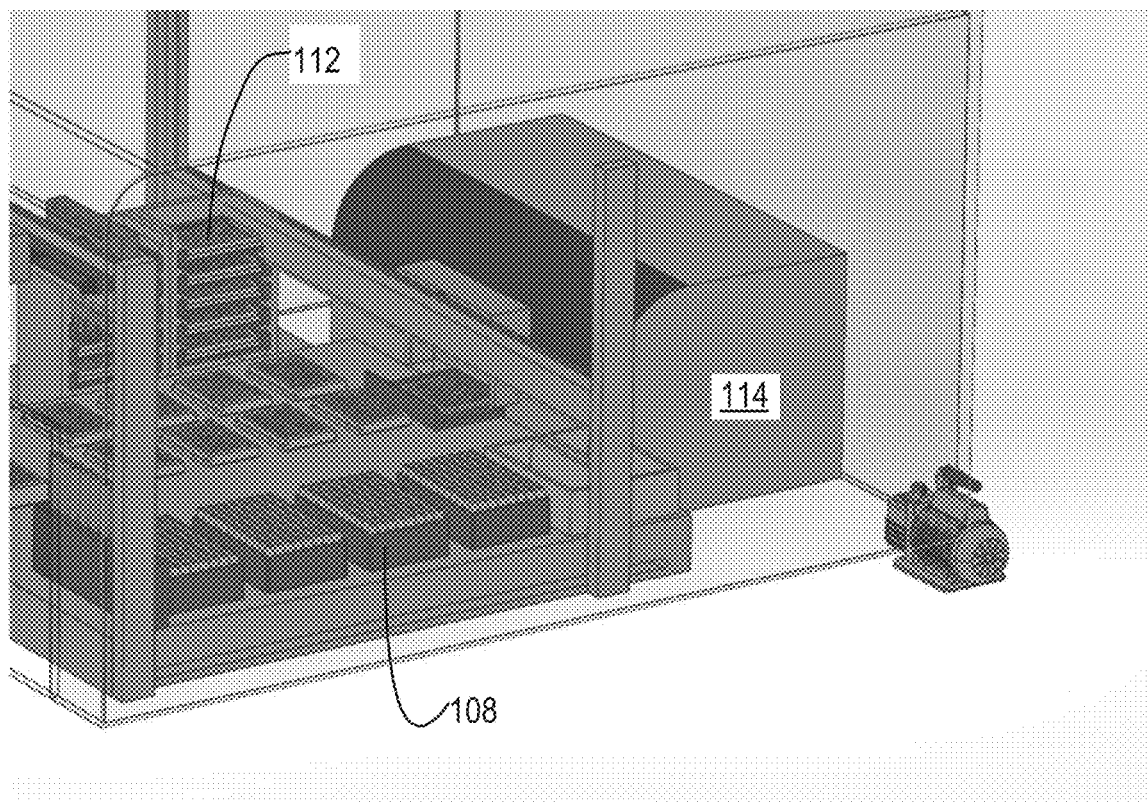
Figure 13:
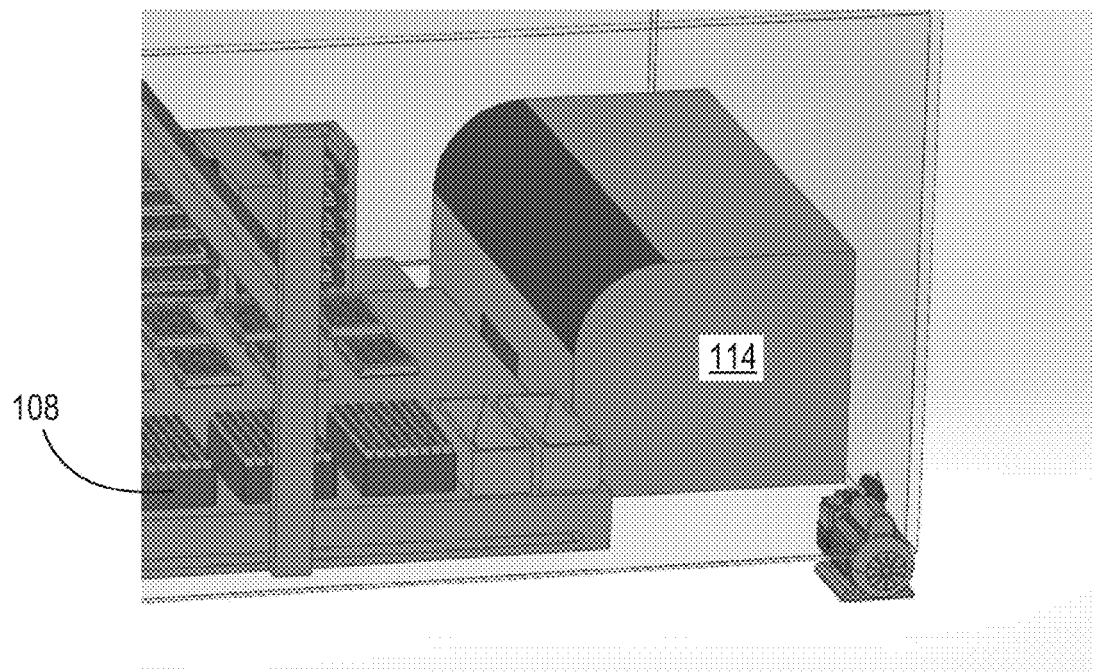

During the sampling mode, the loader 104 can rotate to a position that is substantially perpendicular to the base of the enclosure 102, as illustrated in FIG. 5. During sampling, as illustrated in FIG. 6, a pipette 204 can access the culture inside of the sample vessel 202. The pipette 204 can be coupled to one of the actuators 106, which can position the pipette 204 over the sample vessel 202. In some implementations, the pipette 204 can dispenses the sample from the pipette 204 into a trough 206, as illustrated in FIG. 7. From the trough 206, sampling pipettes can distribute the sample to multiwell plates. In some implementations, the contents of the pipette 204 can be passed to the filtering system 116.

The system 100 can repeatedly alternate between growth modes and sample modes for any given sample to enable data streaming. Data streaming for a sample can include generating multiple sets of output data for a given sample at different time points. Each set of output data can be generated under different experimental conditions. For example, the different samples can be exposed to a different concentration of a given antibiotic.

The filtering system 116 can filter the sample to remove undesired particles, cells, or other material from the sample. The filtering system can remove assay inhibitors from the sample. For example, for a blood-based sample, the filtering system 116 can remove blood cells from the sample and leave bacteria cells within the sample. The filtering system 116 can use acoustophoresis, membrane-based filtering, chemical-based filtering, or a combination thereof. For example, during a first stage of filtering, the filtering system 116 can use acoustophoresis and apply a standing acoustic wave to the sample. The acoustic wave can drive the blood cells and bacteria to different nodes of the acoustic wave such that the blood cells can flow out of a first channel outlet and the bacteria can flow out of a second channel outlet. In some implementations, acoustophoresis can remove about 90% of the blood cells from the sample. In some implementations, the non-ionic detergents (e.g., triton-x) can be added to the output of the acoustophoresis to solubilize the blood cells (or other mammalian cells) while leaving the bacterial cells alive. In some implementations, the sample can be passed a cell trapping device, such as a filter or membrane, to trap the cells. The trapped cells can be removed from the trapping device prior to testing or can be tested while on or within the trapping device. In some implementations, a filter can be used to remove plasma from a blood sample.

Once filtered, the sample can be transferred to multiwell plates. In some implementations, the wells of the plate can also include a filter to filter out or capture particles or cells. The articulators 106 can include automated liquid handling pipettes that can transfer the sample to the multiwell plates. For example, the liquid handling pipets can retrieve a fresh tip from the additional tips and move the sample from the filtering system 116 (or trough 206) to the multiwell plates. The plates can be positioned on the plate deck 110. The articulators 106 can include a plate gripper that can move the plates from the plate deck 110 to the hotel incubator 112.

The hotel incubator 112 can include a plurality of slots 208. The hotel incubator 112 can be configured to hold or store a plurality of multiwell plates. For example, a plate can be stored into each of the slots. Each slot can be heated. For example, the bottom surface of each slot 208 can include a heating element that warms the contents of the multiwell pate in the given slot 208. The bacteriophage can be applied to the samples placed in the multiwell pate. More information about the bacteriophage and testing process can be found in Appendix B of this document. At the end of the reaction time with the bacteriophage, the articulators 106 can move the plate into the testing system 114 where light emitted from the sample can be measured. The testing system 114 can also apply a strong chemical quench or reaction to kill the bacteria and other cells in the sample.

Figure 14:
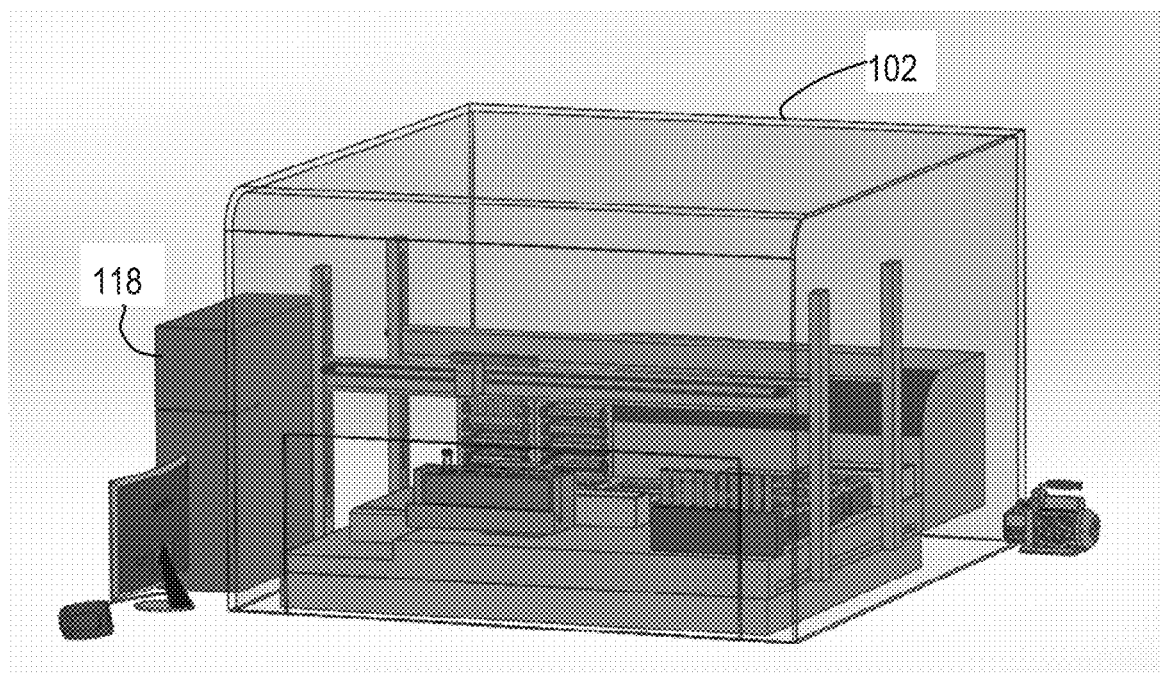

The system 100 can include a controller 118. The controller 118 can be an application specific integrated circuit (ASIC). The controller 118 can be a data processing system or a component thereof. For example, the controller 118 can be a desktop computer, laptop computer, tablet computer, mobile phone, or special purpose logic. In FIG. 14, the controller 118 is illustrated as a desktop computer.

The controller 118 can control when the loader 104 transitions between the growth mode and the sampling model. The controller 118 can control the movement and actions of the articulators 106. The controller 118 can control the testing system 114. The controller 118 can receive the output data from the testing system 114 and can perform analysis on the output data to determine, for example, whether an antibiotic applied to the sample was affective or whether the sample includes bacteria. The controller 118 can run interpretative algorithms on the output data and produce a report describing identifications and antibiotic susceptibility profile.

The controller 118 can control the environmental control system 120. For example, the controller 118 can set the pressure differential that the environmental control system 120 maintains between the interior and exterior of the enclosure 102.

The controller 118 can include or can interface with a screen and other inputs that enable a user to set the conditions within the enclosure 102. Via the interface the displayed on the screen, the user can log samples into the system 100, set when tests should be run, the intervals between tests, and set what tests should be run on each of the samples.

The controller 118 can interface with a scanner 122. In some implementations, each of the sample vessels 202 can include a barcode or other machine readable label. A user can scan the barcode with the scanner 122 to log the sample into the system. For example, processing the barcode, the controller 118 can log a patient identifier into a database maintained by the controller 118. With the entry, the controller 118 can add a time the sample was added to the system 100. Data from the testing system 114 that is generated from the processing of the sample can be stored by the controller 118 into the database in association with the patient identifier.

The controller 118 can also include and track other metadata for a given sample. The metadata can include a patient sample id; position, amount, and concentrations of the antibiotics used for tests; and reporter phage identifiers. The reporter phage in some instances would be lumi-phage. The controller 118 can also track the times of sample growth and incubation times.

The controller 118 can perform scheduling of the movements, actions, and tests of the system 100. For example, different samples can be added to the loader 104 at different times. The controller 118 can generate a schedule for each of the samples. The schedule can indicate the times at which actions (e.g., movement of a multiwell pate is moved from the hotel incubator 112 to the plate deck 110 or drawing of samples from the sample vessel 202) or tests are performed by the system 100. The controller 118 can resolve conflicts in the schedules of the different samples. One example conflict is that two different samples are scheduled to be processed with the testing system 114 at the same time. The controller 118 can resolve the conflict by adjusting the time at each of the actions or tests are performed. In some implementations, when a new sample is added, the controller 118 can compare the candidate schedule to the schedules of each of the samples already active in the system 100. The controller 118 can determine if the candidate schedule conflicts with any of the schedules of each of the samples already active in the system 100. If a conflict exists, the controller 118 can adjust (or recommend an adjustment) to the start time of the schedule generated for the new sample. Adjusting the start time of the schedule, rather than the timing of individual steps within the schedule, can enable the time between neighboring steps to remain consistent. For example, rather than adjusting an incubation time from 45 minutes to 40 minutes to avoid a conflict, adjusting the start time can enable the incubation time to remain at 45 minutes.

Figure 15:
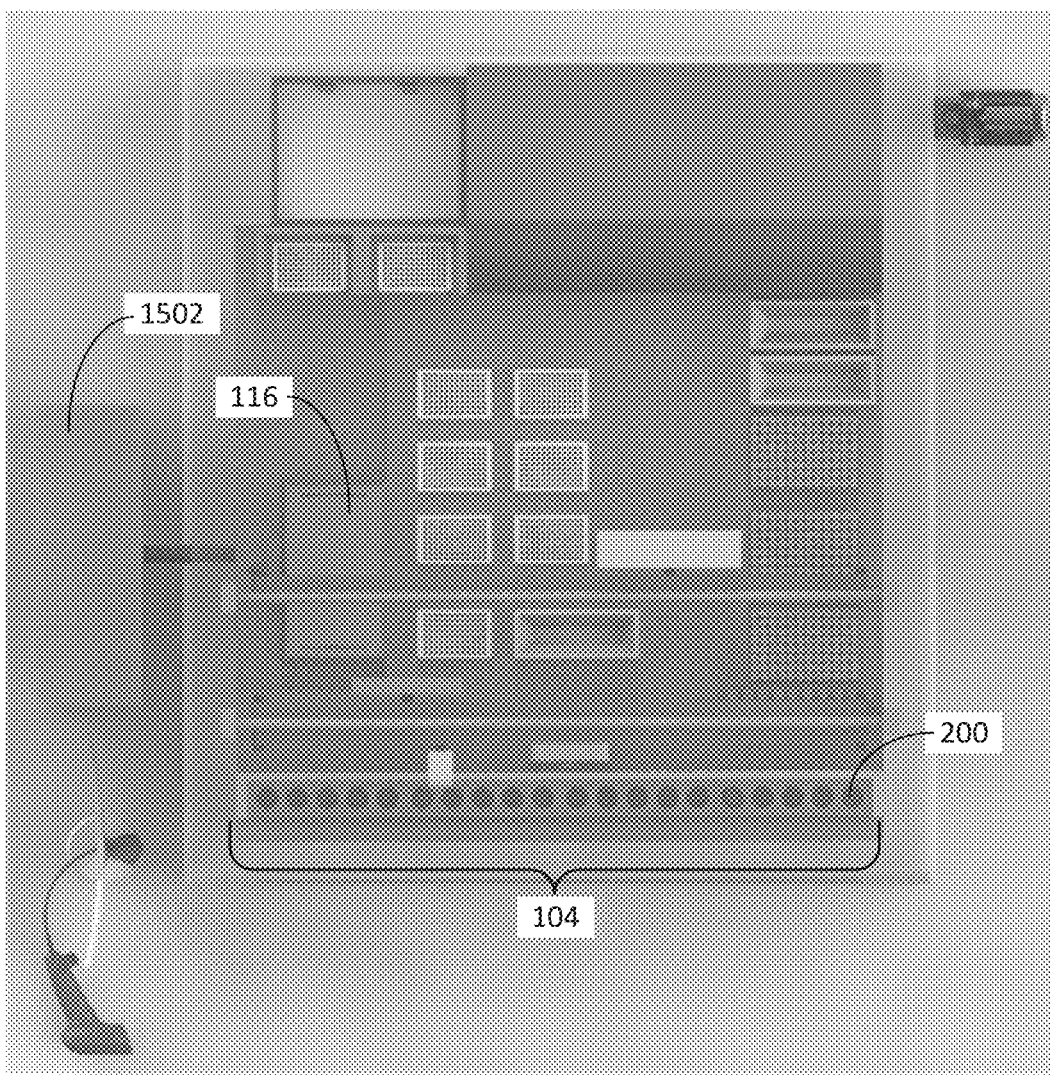

FIG. 15 illustrates a top-down view of an example implementation of the system 100 of FIG. 1. As shown in FIG. 15, the system 100 may include a loader 104 having more sample slots 200 than are shown in other example implementations, such as those depicted in FIGS. 3 and 4. For example, as shown in FIG. 15, the loader 104 may include at least 20 sample slots 200, each of which may be configured to receive a respective sample vessel 202. FIG. 15 also depicts a power supply 1502. The power supply 1502 can be coupled with the filtering system 116. The filtering system 116 may also be referred to as a sample purifier. The power supply 1502 can be configured to supply electrical power to the filtering system 116. For example, electrical power from the power supply 1502 can be used by the filtering system 116 (or a component thereof) to generate one or more acoustic waves that can be used to implement acoustophoresis for separating undesired particles from the sample fluid.

Figure 16:
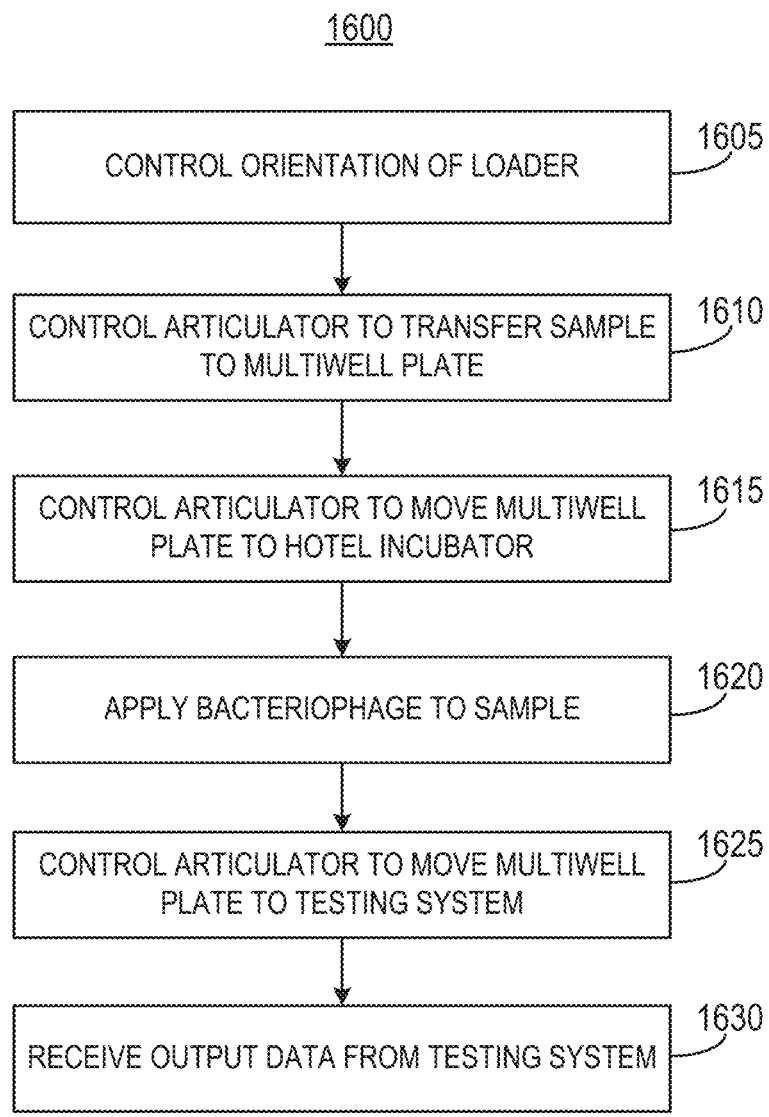
FIG. 16 illustrates a flowchart of a method for testing fluid samples, according to an illustrative implementation.

FIG. 16 illustrates a flowchart of an example method 1600 for testing fluid samples, according to an illustrative implementation. In some implementations, the method 1600 can be performed using a system such as the system 100 depicted in FIG. 1. For example, at least some of the steps of the method 1600 can be performed by a controller such as the controller 118 of the system 100. FIGS. 17-28 illustrate various views of the system 100 of FIG. 1 in the stages of the method 1600 of FIG. 16, according to illustrative implementations. Accordingly, FIG. 16 and FIGS. 17-28 are described together below.

Figure 17:
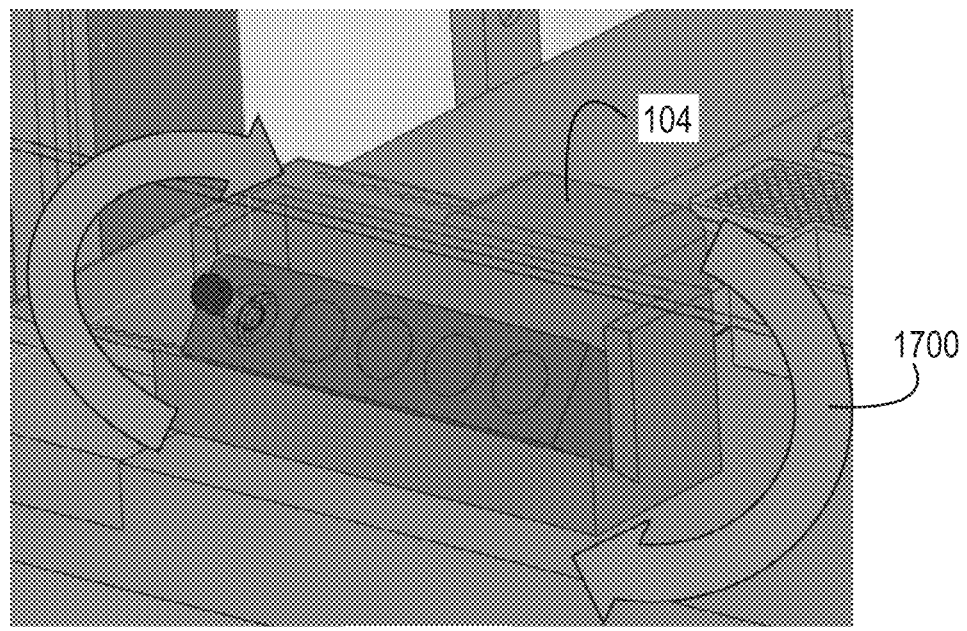
FIGS. 17-28 illustrate various views of the system of FIG. 1 in the stages of the method of FIG. 16, according to illustrative implementations.
Figure 18:
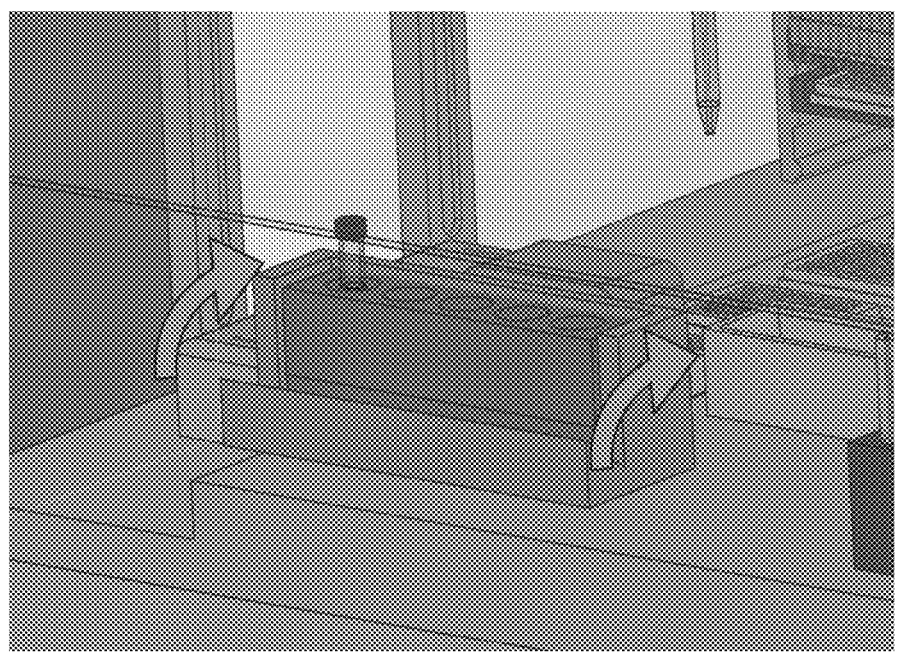
Figure 19:
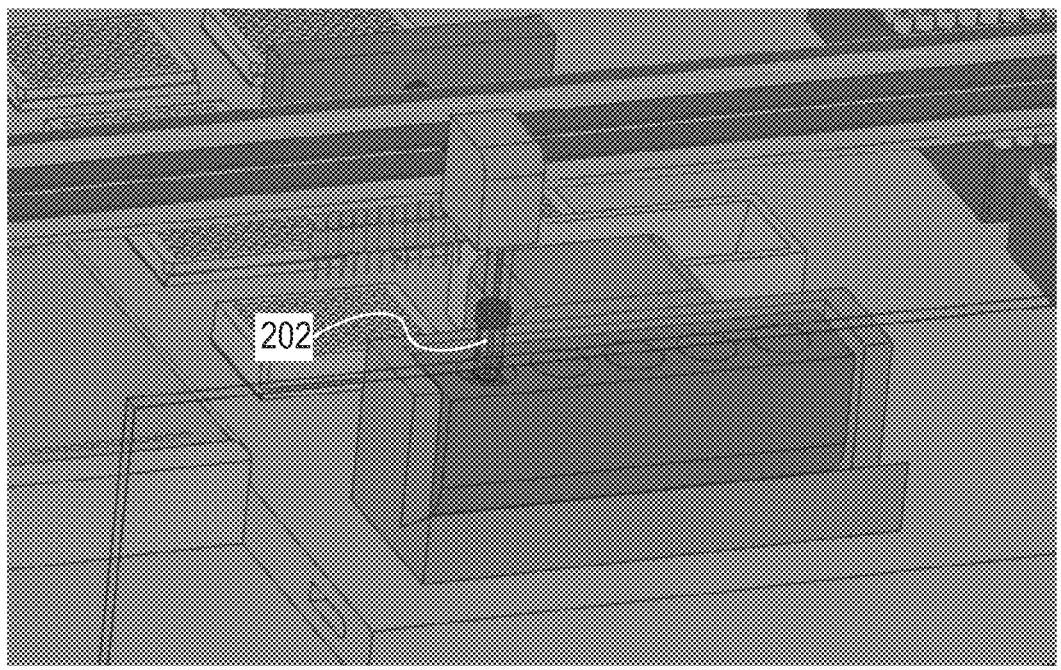
Figure 20:
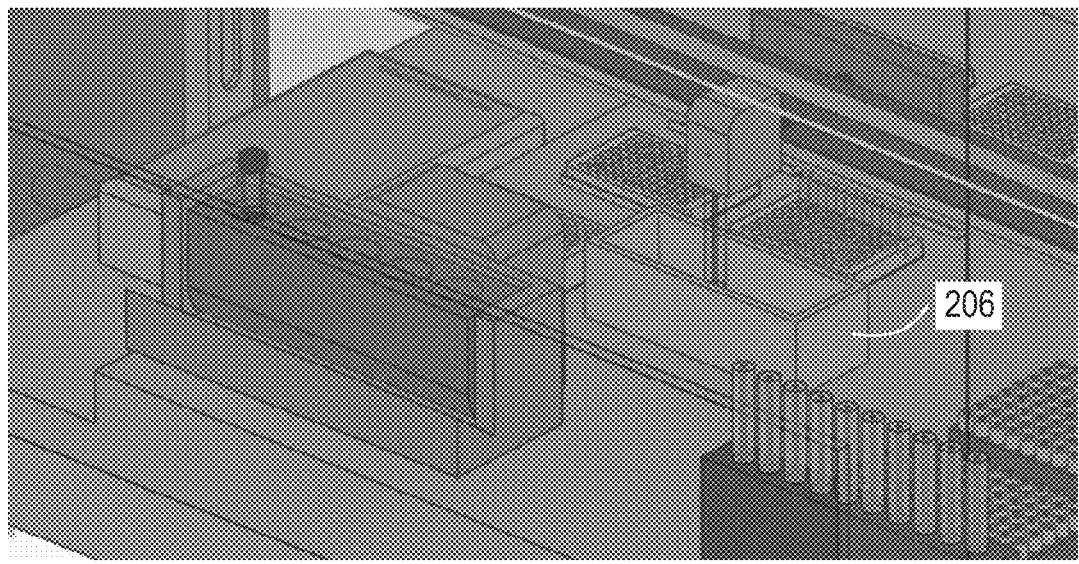

Referring now to FIG. 16, the method 1600 can include controlling an orientation of the loader 104 (stage 1605). For example, the controller 118 can control the loader 104 to position or orient the loader at an angle that corresponds to a first predetermined tilt angle with respect to a base of the enclosure 102. In some implementations, the predetermined tilt angle can be 45 degrees. In some implementations, the predetermined tilt angle can be in the range of 40 degrees to 50 degrees, in the range of 35 degrees to 40 degrees, or in the range of 50 degrees to 55 degrees. FIGS. 17-19 illustrate enlarged views of the loader 104. As illustrated in FIG. 17, the loader 104 is in the growth mode or growth configuration. In the growth mode, the loader 104 is tilted at the first predetermined tilt angle. The loader 104 can include an orbital shaker. As illustrated by the arrows 1700, the loader 104 can apply an orbital rotation to the sample vessels 202 within the loader 104 for at least a portion of the growth mode. The rotation can enable aeration of the sample. The loader 104 can include a tunable controller that can be controlled directly or via the controller 118 to control the speed and amount of agitation applied by the loader's shaker, as well as to orient the loader 104 at the first predetermined tilt angle for the growth phase.

The method 1600 can include controlling the articulators 106 to transfer the fluid sample to a multiwell plate (stage 1610). For example, an articulator 106 can transfer the fluid sample from the sample vessel to at least one well the multiwell plate. In some implementations, the multiwell plate can be positioned on plate deck 110 within the enclosure 102. In some implementations, as depicted in FIG. 18, the loader 104 can first be rotated to a second predetermined tilt angle for the sampling mode or configuration. For example, the second predetermined angle can be an angle at which the loader 104 (and the sample vessel 202) is perpendicular to the base of the enclosure 102. As illustrated in FIG. 19, when in the sampling mode, a pipette coupled with the articulators 106 can be lowered into the sample vessel 202 to collect a portion of the fluid sample therein.

Figure 21:
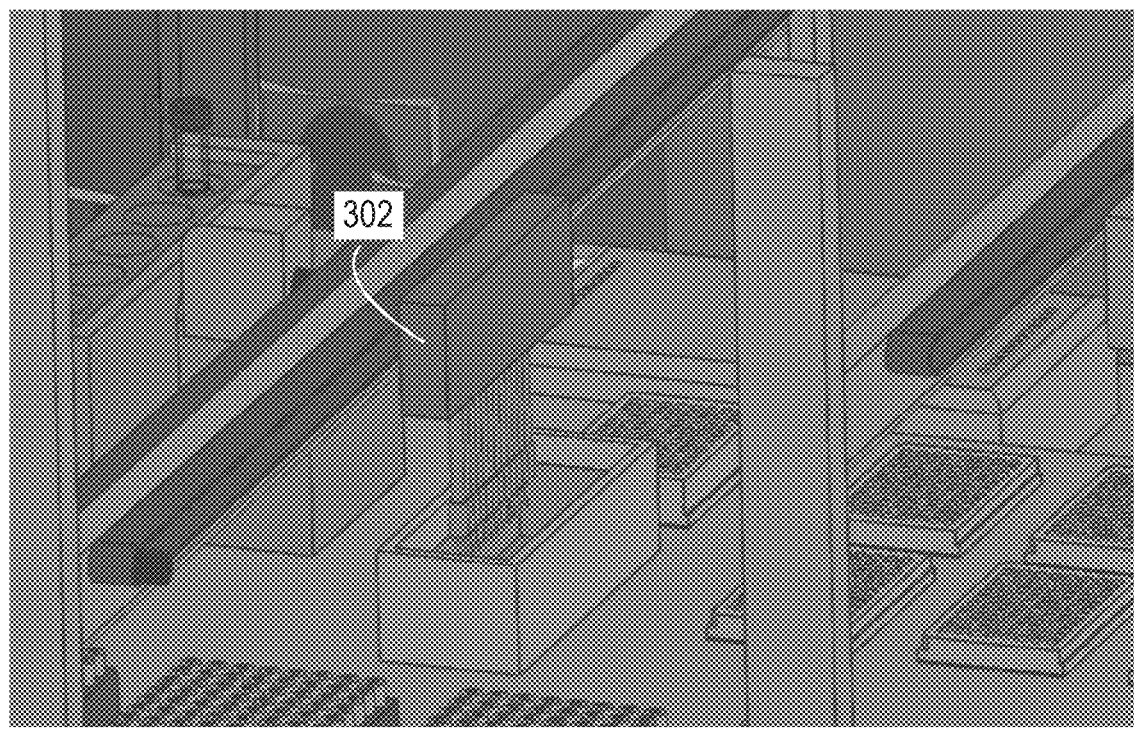
Figure 22:
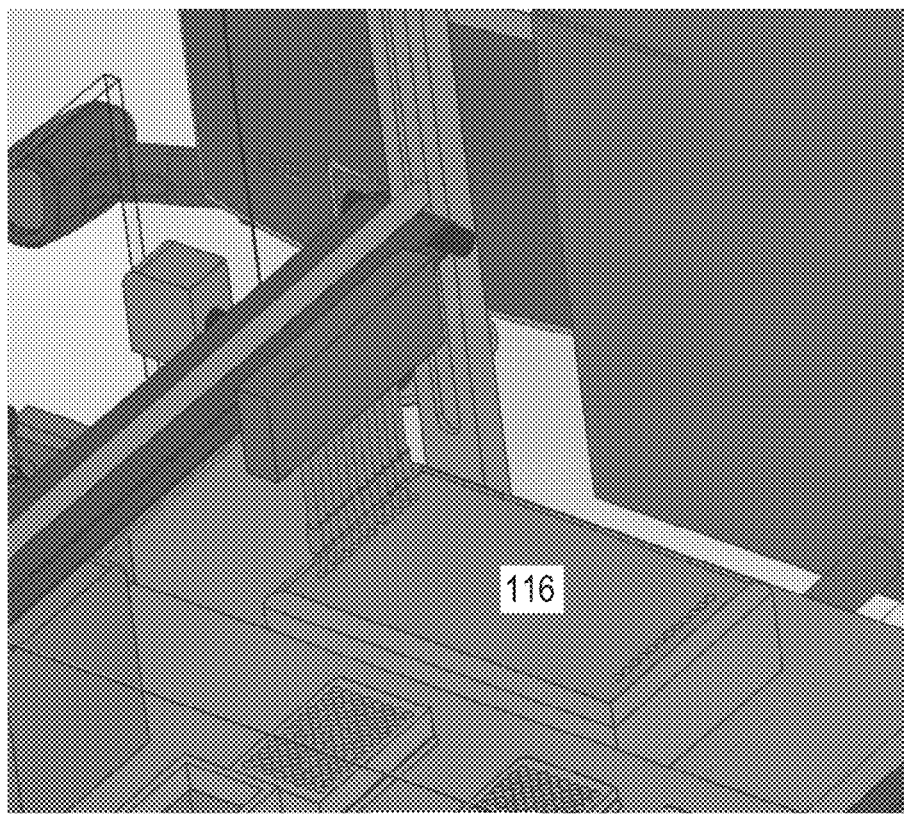
Figure 23:
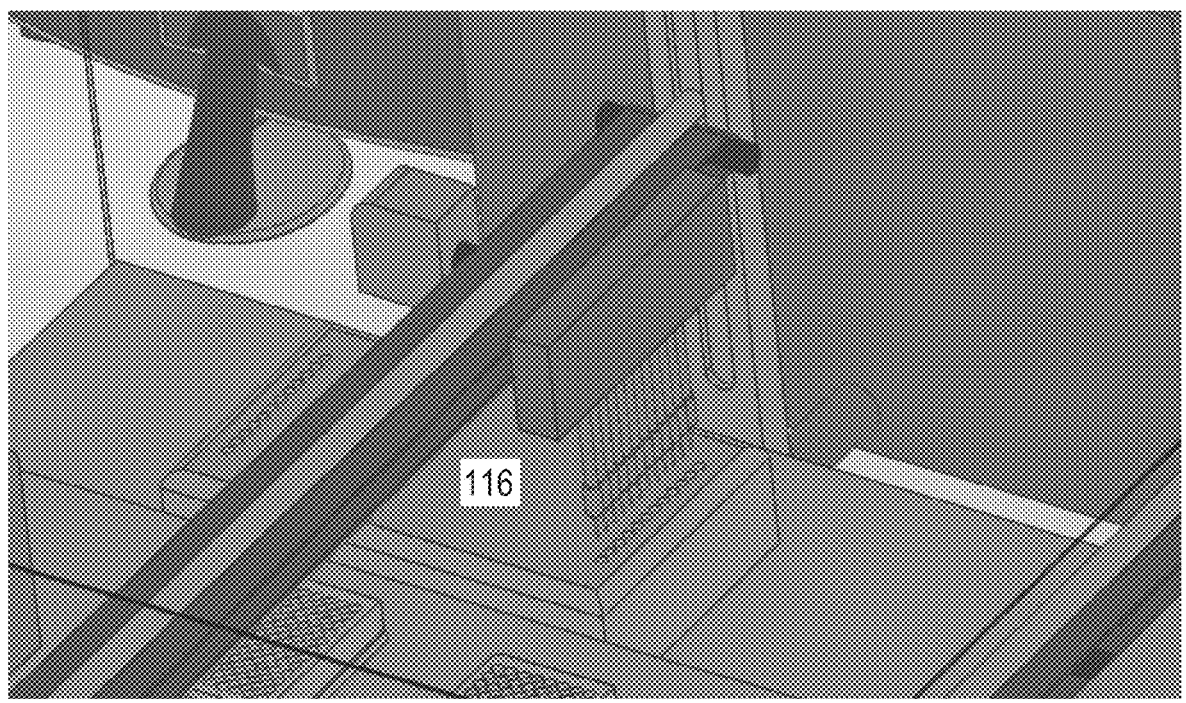
Figure 24:
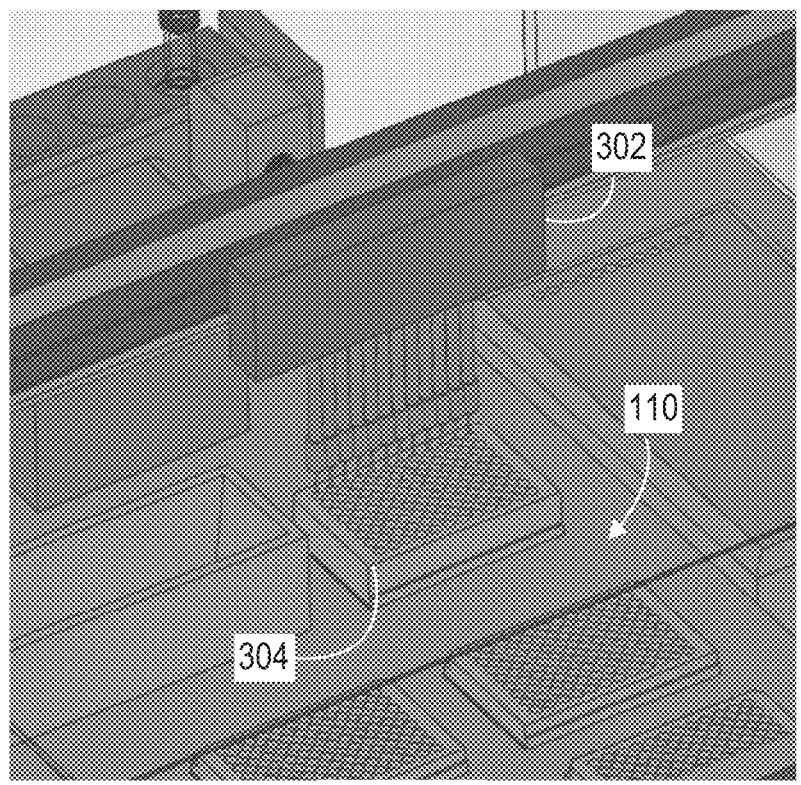

In some implementations, the articulator 106 can move the fluid sample directly from the sample vessel 202 in the loader 104 to the well plate. In some other implementations, the fluid sample may be processed, for example to remove undesired particles, before being moved to the well plate. For example, as show in FIG. 20, the pipette can move the collected sample from the sample vessel 202 to the loading trough 206. FIG. 21 illustrates a multichannel pipette 302 loading the fluid sample from the loading trough 206. As illustrated in FIG. 22, the multichannel pipette 302 can load the sample into the inlets of the filtering system 116. The multichannel pipette 302 can collect the enriched sample (e.g., the sample with blood cells removed) from the outlets of the filtering system 116, as illustrated in FIG. 23. The multichannel pipette 302 can discard and then retrieve fresh tips from the additional tips 108 between interactions with the sample. FIG. 24 illustrates the multichannel pipette 302 moving the enriched sample from the outlets of the filtering system 116 to a multiwell plate 304.

Figure 25:
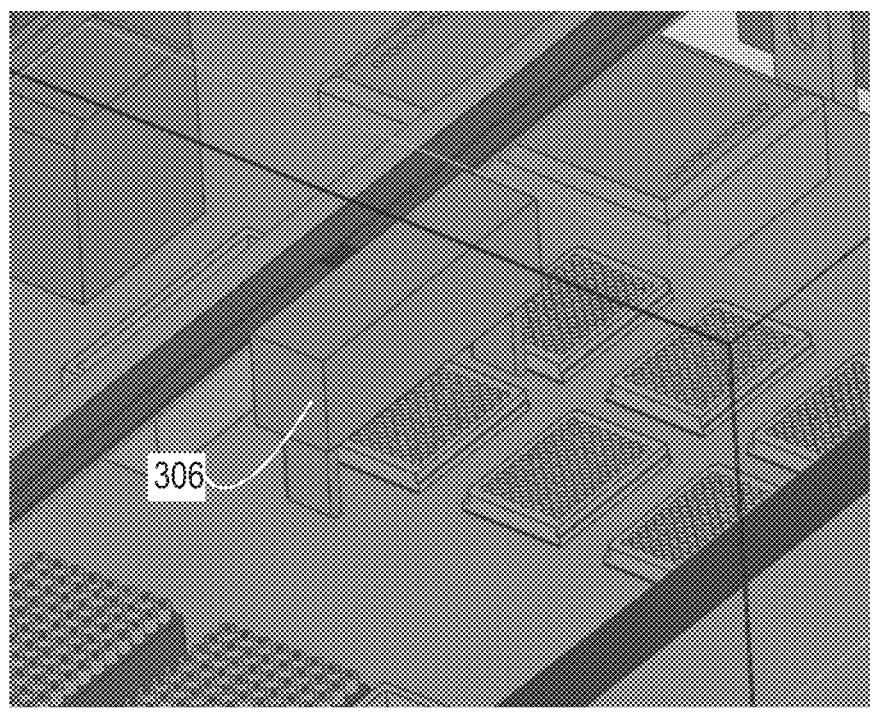
Figure 26:
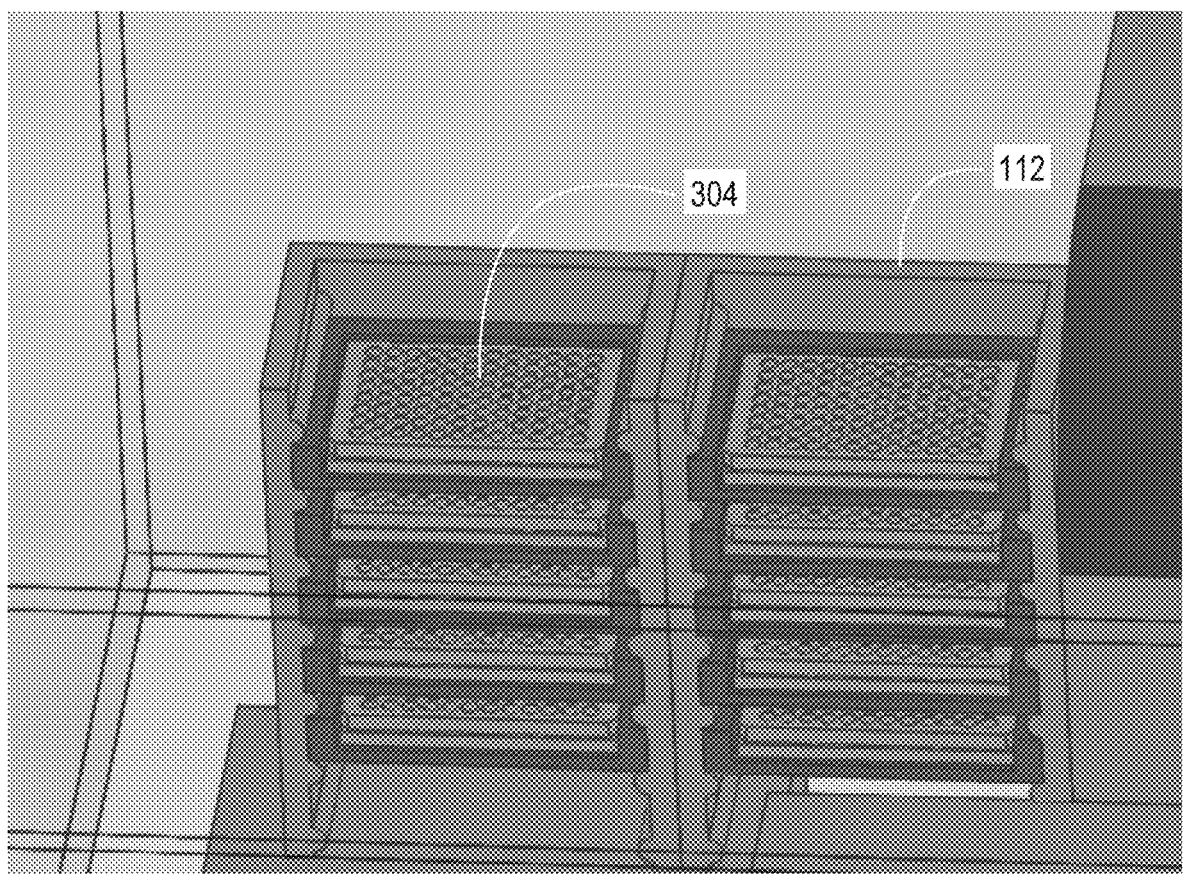

The method 1600 can include controlling the articulator 106 to move the multiwell plate 304 from the plate deck 110 to the hotel incubator 112 (stage 1615). For example, once the sample is loaded into the plate 304, the articulator's plate gripper 306 can grab and move the plate 304 to the hotel incubator 112, as illustrated in FIG. 25. FIG. 26 illustrates an enlarged view of the hotel incubator 112 after the plate 304 is inserted into one of the hotel incubator's slots. In some implementations, the hotel incubator 112 can extend a platform from each of the slots such that the plate gripper 306 can load the plate 304 onto the platform. The hotel incubator 112 can then retract the platform into the slot.

The method 1600 can include applying a bacteriophage to the fluid sample (stage 1620). In some implementations, the bacteriophage can be a lumi-phage configured or selected to emit light. In some implementations, the plate 304 can be preloaded with bacteriophage. Thus, the bacteriophage can be added to the fluid sample when the fluid sample is introduced into the plate 304. In some implementations, the plate 304 can also be preloaded with one or more antibiotics. In some other implementations, the bacteriophage and one or more antibiotics may be applied to the fluid sample after the fluid sample has been introduced into the plate 304. For example, in some implementations the system 100 can include an automatic fluid handling system that can dispense the antibiotics and/or bacteriophage into the wells of the plate 304 before or after the sample is added to the wells.

Figure 27:
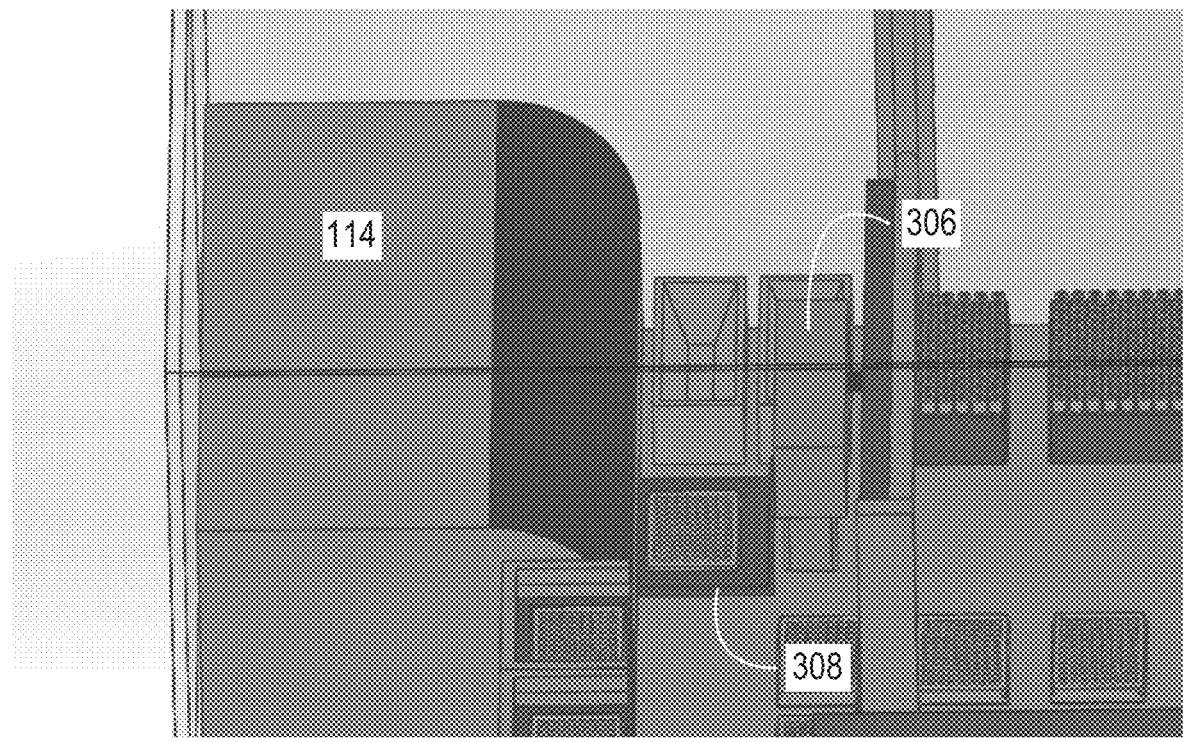
Figure 28:
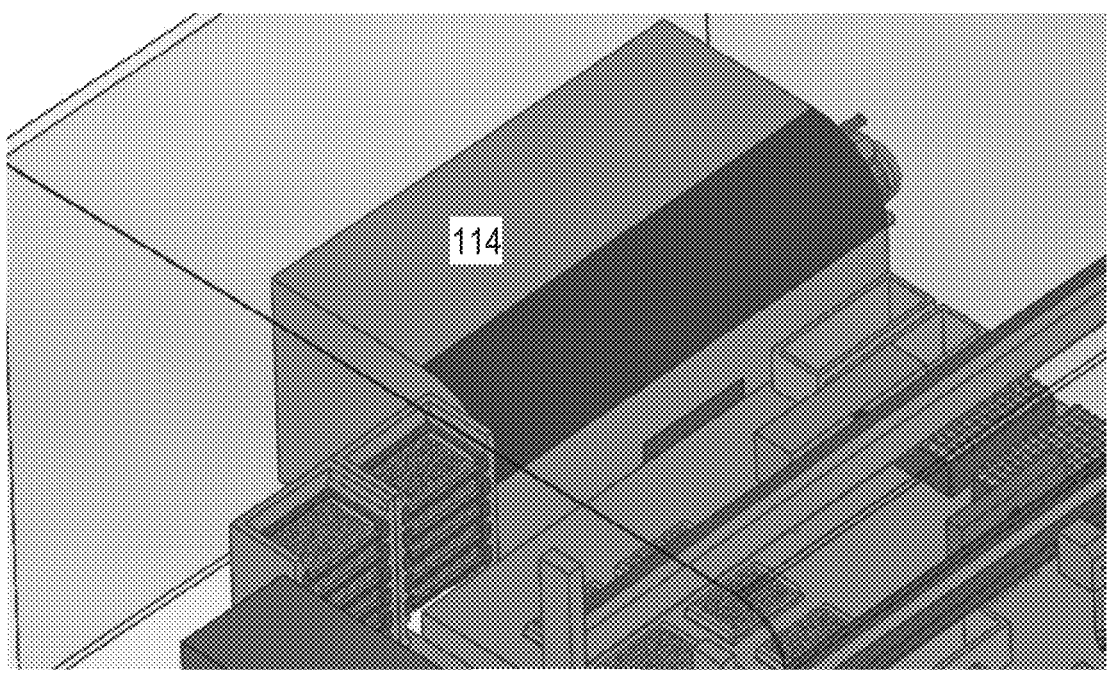

The method 1600 can include controlling the articulator to move the multiwell plate 304 from the hotel incubator 112 to the testing system 114 (stage 1625). For example, the plate 304 can be moved to the testing system 114 after a predetermined amount of time (e.g., a reaction time). In some implementations, the plate gripper 306 can move the plate 304 from the hotel incubator 112 to the testing system 114. The testing system 114 can extend a loading tray 308 onto which the plate gripper 306 can deposit the plate 304, as depicted in FIG. 27. The testing system 114 can retract the loading tray 308 into the body of the testing system 114, as depicted in FIG. 28.

The method 1600 can include receiving output data from the testing system 114 (stage 1630). For example, the output data can be received by the controller 118. For example, the testing system 114 can observe, determine, or identify characteristics of the fluid sample, such as by measuring light emitted from the sample (e.g., via the lumi-phage). The testing system 114 can also generate output data representative of the observed, determined, identified, or measured characteristics of the fluid sample. The controller 118 can receive the output data from the testing system 114 and can perform analysis on the output data to determine, for example, whether an antibiotic applied to the sample was effective, whether the sample includes bacteria, an amount of bacteria included in the sample fluid after testing, and the like. The controller 118 can run interpretative algorithms on the output data and produce a report describing identifications and antibiotic susceptibility profile.

Thus, using the system 100 described herein, accurate identification of bacterial species within a biological sample can inform the selection of suitable therapies for treating bacterial infections. Recombinant detector bacteriophages may be used to identify bacteria present within a fluid sample (e.g., whole blood, plasma, serum). Such methods entail contacting the biological sample with a recombinant detector bacteriophage, and detecting the presence of bacterial host cells infected by the recombinant detector phage, wherein the recombinant detector phage comprises a heterologous nucleic acid that encodes a detectable gene product, thereby leading to the identification of bacteria present within the biological sample.

Additionally or alternatively, recombinant detector bacteriophages may be used in methods for profiling antibiotic susceptibility of bacteria present within a biological sample (e.g., whole blood, plasma, serum). The profiling of antibiotic susceptibility can be used with the system 100. For example, a method can include (a) contacting the biological sample with an antibiotic and a recombinant detector bacteriophage, (b) detecting the presence of bacterial host cells infected by the recombinant detector phage, wherein the recombinant detector phage can include a heterologous nucleic acid that encodes a detectable gene product, and (c) determining that the antibiotic is effective in inhibiting the bacteria present in the biological sample when the number of recombinant detector phage infected bacterial host cells is reduced relative to that observed in an untreated control sample.

In one aspect, the present disclosure provides a method for identifying at least one bacterial strain or species in a test sample obtained from a subject comprising (a) separating bacterial cells isolated from the test sample into one or more sub-samples, (b) contacting each sub-sample with one or more recombinant detector bacteriophages as disclosed herein, wherein each recombinant detector bacteriophage comprises a heterologous nucleic acid encoding one or more reporter genes, and (c) identifying at least one bacterial strain or species in the test sample by detecting the expression of the one or more reporter genes of the one or more recombinant detector bacteriophages. In certain embodiments, the method for identifying at least one bacterial strain or species in a test sample does not require the culturing of bacterial cells from the test sample or a sub-sample.

In some embodiments, identification of at least one bacterial strain or species includes detecting the expression of the one or more reporter genes of the one or more recombinant detector bacteriophages, e.g., detection of green fluorescence indicates the presence of bacterial species A whereas detection of blue fluorescence indicates the presence of bacterial species B. In some embodiments, the absence of at least one bacterial strain or species is identified by the lack of detectable expression of the one or more reporter genes of the one or more recombinant detector bacteriophages, e.g., undetectable expression of green fluorescence indicates the lack of bacterial species A in a test sample or sub-sample. These methods can be used in combination with the system 100.

In some embodiments, the one or more recombinant detector bacteriophages infect a single species of bacteria. In certain embodiments, the one or more recombinant detector bacteriophage infect two or more species of bacteria. By way of example, but not by way of limitation, in some embodiments, the species of bacteria that are infected include *Pseudomonas aeruginosa, Escherichia coli, Staphylococcus aureus, Klebsiella pneumoniae, Yersinia pestis, Bacillus anthracis, Burkholderia mallei*, and *Franciscella tularensis*. These methods can be used in combination with the system 100.

In some embodiments, the one or more recombinant detector bacteriophages that infect two or more species of bacteria comprise different reporter genes, wherein the recombinant detector bacteriophages that infect the same species of bacteria comprise the same reporter gene(s). In some embodiments, detection of the expression of the reporter gene is detection of the gene product itself, e.g., a fluorescent protein. In some embodiments, detection of the expression of the reporter gene is detection of an enzymatic reaction requiring the expression of the reporter gene, e.g., expression of luciferase to catalyze luciferin to produce light.

In some embodiments, the expression of the one or more reporter genes is detected in about 5, 10, 15, 20, 25, 30, 35, 40, 45, 50, 55, 60, 65, 70, 75, 80, 85, 90 minutes or any time between any two of the preceding values after contacting a sub-sample with the one or more recombinant detector bacteriophages using the system 100.

In another aspect, the present disclosure provides a method for determining the antibiotic susceptibility of a bacterial strain or species in a test sample obtained from a subject comprising (a) separating bacterial cells isolated from the test sample into a plurality of sub-samples, (b) contacting the plurality of sub-samples with a recombinant detector bacteriophage and at least one antibiotic, wherein the recombinant detector bacteriophage comprises a heterologous nucleic acid encoding a reporter gene, and (c) detecting the expression of the reporter gene of the recombinant detector bacteriophage in the presence of each antibiotic. In some embodiments, the method further includes determining that the bacterial strain or species in the test sample is susceptible to an antibiotic if the reporter gene expression of the recombinant detector bacteriophage in the antibiotic treated sub-sample is decreased relative to that observed in a control sub-sample that is not treated with the antibiotic. In other embodiments, the method further comprises determining that the bacterial strain or species in the test sample is resistant to an antibiotic if the reporter gene expression of the recombinant detector bacteriophage in the antibiotic treated sub-sample is comparable to that observed in a control sub-sample that is not treated with the antibiotic. In certain embodiments, the method for determining the antibiotic susceptibility of a bacterial strain or species in a test sample does not require the culturing of bacterial cells from a test sample or a sub-sample. These methods can be used in combination with the system 100.

While operations are depicted in the drawings in a particular order, such operations are not required to be performed in the particular order shown or in sequential order, and all illustrated operations are not required to be performed. Actions described herein can be performed in a different order. For example, in some implementations, the sample may not be passed through the filtering system.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A system for testing a fluid sample, the system comprising:
an enclosure;
a loader positioned within the enclosure and comprising a sample holder configured to hold a sample vessel;
a plate deck positioned within the enclosure and configured to support a multiwell plate comprising a plurality of wells;
a hotel incubator positioned within the enclosure and configured to receive the multiwell plate;

an articulator positioned within the enclosure and configured to manipulate and transfer the fluid sample within the system;
a testing system positioned within the enclosure and configured to identify bacteria in the fluid sample; and
a controller configured to:
  operate the system in a growth mode by controlling an orientation of the loader to correspond to a first predetermined tilt angle with respect to a base of the enclosure to cause the bacteria to grow in the fluid sample within the sample vessel for a predetermined growth time period; and
  operate the system in a sampling mode by:
    controlling the articulator to transfer the fluid sample from the sample vessel to at least one well of the plurality of wells of the multiwell plate;
    controlling the articulator to move the multiwell plate from the plate deck to the hotel incubator;
    applying a bacteriophage to the fluid sample;
    controlling the articulator to move the multiwell plate from the hotel incubator to the testing system after a predetermined reaction time period; and
  receive output data from the testing system, the output data identifying a characteristic of the bacteria in the fluid sample.

2. The system of claim 1, further comprising:
an environmental control system configured to control at least one environmental characteristic within the enclosure.

3. The system of claim 2, wherein:
the environmental control system comprises a vacuum pump; and
the controller is further configured to control the vacuum pump to maintain a predetermined pressure within the enclosure.

4. The system of claim 2, wherein:
the environmental control system comprises a gas pump; and
the controller is further configured to control the gas pump to circulate a gas within the enclosure.

5. The system of claim 1, wherein:
the controller is further configured to control the orientation of the loader to correspond to a second predetermined tilt angle, different from the first predetermined tilt angle, with respect to a base of the enclosure during the sampling mode.

6. The system of claim 5, wherein the second predetermined tilt angle of the loader is perpendicular to the base of the enclosure.

7. The system of claim 1, wherein:
the loader further comprises a shaker; and
the controller is further configured to cause the shaker to vibrate the sample holder to agitate the fluid sample during the growth mode.

8. The system of claim 1, wherein the articulator further comprises an automated liquid handling pipette to transfer the fluid sample from the sample holder to the at least one well of the plurality of wells of the multiwell plate.

9. The system of claim 1, wherein the articulator further comprises a plate gripper to move the multiwell plate from the plate deck to the hotel incubator.

10. The system of claim 1, wherein the hotel incubator further comprises:
at least one slot configured to receive the multiwell plate; and
a heating element coupled with the at least one slot and configured to apply heat to multiwell plate within the at least one slot.

11. The system of claim 1, wherein:
the bacteriophage comprises a lumi-phage; and
the testing system is configured to measure light emitted by the bacteriophage.

12. The system of claim 1, further comprising a filtering system configured to receive the fluid sample and to remove particles from the fluid sample.

13. The system of claim 12, wherein the controller is further configured to cause the filtering system to remove the particles from the fluid sample using at least one acoustophoresis, membrane-based filtering, or chemical filtering.

14. The system of claim 1, further comprising an antibiotic within the at least one well of the multiwell plate, wherein the controller is further configured to process the output data received from the testing system to determine a response of the bacteria to the antibiotic.

15. The system of claim 1, wherein the fluid sample comprises a first fluid sample, and wherein the controller is further configured to cause the system to process a second fluid sample simultaneously with the first fluid sample.

16. A method of testing a fluid sample, the method comprising:
controlling, by a controller comprising at least one processor, an orientation of a loader comprising a sample holder configured to hold a sample vessel to correspond to a first predetermined tilt angle with respect to a base of an enclosure to cause bacteria to grow in the fluid sample during a predetermined growth time period;
controlling, by the controller, an articulator to transfer the fluid sample from the sample vessel to at least one well of a plurality of wells of a multiwell plate positioned on a plate deck within the enclosure;
controlling, by the controller, the articulator to move the multiwell plate from the plate deck to a hotel incubator within the enclosure;
applying a bacteriophage to the fluid sample;
controlling, by the controller, the articulator to move the multiwell plate from the hotel incubator to a testing system within the enclosure after a predetermined reaction time period; and
receiving, by the controller, output data from the testing system, the output data identifying a characteristic of the bacteria in the fluid sample.

17. The method of claim 16, further comprising:
controlling, by the controller, an environmental control system configured to control at least one environmental characteristic within the enclosure.

18. The method of claim 17, wherein the environmental control system comprises a vacuum pump, and wherein the method further comprises controlling the vacuum pump to maintain a predetermined pressure within the enclosure.

19. The method of claim 17, wherein the environmental control system comprises a gas pump, and wherein the method further comprises controlling the gas pump to circulate a gas within the enclosure.

20. The method of claim 16, wherein the loader further comprises a shaker, and wherein the method further comprises causing the shaker to vibrate the sample holder to agitate the fluid sample during the growth mode.

* * * * *